United States Patent [19]
Bergman et al.

[11] Patent Number: 5,181,919
[45] Date of Patent: Jan. 26, 1993

[54] SUTURE LIGATING DEVICE FOR USE WITH AN ENDOSCOPE

[76] Inventors: Arieh Bergman, 439 S. LaPeer Ave., Beverly Hills, Calif. 90211; Amos Freedy, 16943 Encino Hills Dr., Encino, Calif. 91436; Michael Vermesh, 18142 Sandringham Ct., Northridge, Calif. 91326

[21] Appl. No.: 690,115

[22] Filed: Apr. 23, 1991

[51] Int. Cl.⁵ .............................................. A61B 17/00
[52] U.S. Cl. ..................................... 606/144; 606/139
[58] Field of Search ............... 606/139, 144, 145, 146, 606/151

[56] References Cited

U.S. PATENT DOCUMENTS

| | | | |
|---|---|---|---|
| 3,570,497 | 3/1971 | Lemole | 606/224 |
| 3,985,138 | 10/1976 | Jarvik | 606/144 |
| 4,069,825 | 1/1978 | Akiyama | 606/158 |
| 4,493,323 | 1/1985 | Albright et al. | |
| 4,596,249 | 6/1986 | Freda et al. | |
| 4,602,635 | 7/1986 | Mulhollan et al. | 606/144 |
| 4,621,640 | 11/1986 | Mulhollan et al. | 606/144 |
| 4,683,885 | 8/1987 | Hutterer et al. | 606/224 |
| 4,932,962 | 6/1990 | Youn et al. | 606/224 |
| 4,957,498 | 9/1990 | Caspari et al. | 606/144 |
| 4,981,149 | 1/1991 | Yoon et al. | 606/224 |
| 4,997,436 | 3/1991 | Oberlander | 606/139 |
| 5,015,249 | 5/1991 | Nakao et al. | 606/142 |
| 5,037,433 | 8/1991 | Wilk et al. | 606/144 |
| 5,059,201 | 10/1991 | Asnis | 606/144 |

*Primary Examiner*—Stephen C. Pellegrino
*Assistant Examiner*—Gary Jackson
*Attorney, Agent, or Firm*—W. Edward Johansen

[57] ABSTRACT

A suture ligating device for use with an endoscope includes a long hollow tube and an elongated, integral member, a resiliently-biased scissoring mechanism, a suture carrying mechanism and a suture grasping mechanism. The long hollow tube has a open end which has a inwardly beveled edge and a closed end and is adapted to be slidably inserted into the endoscope. The elongated, integral member is adapted to be slidably inserted into the long hollow tube through the open end and is shaped like a fork having a stem having a first end and a second end. A first elongated prong has a first end and a second end. A second elongated prong has a first end and a second end. The first and second prongs are joined at the respective first ends thereof to the stem at its first end. One scissor arm of the resiliently-biased scissoring mechanism is fixedly coupled to the long hollow tube at its closed end and the other scissor arm is pivotally coupled to the long hollow tube at its closed end in order to be able to retract the elongated, integral member from a first position. The suture grasping mechanism and the suture carrying mechanism are mechanically coupled to the first and second prongs at their second ends and are aligned so that they become engaged when the elongated, integral member is retracted from the first position to a second position so that a slip knot can be tied externally to the endoscope.

1 Claim, 1 Drawing Sheet

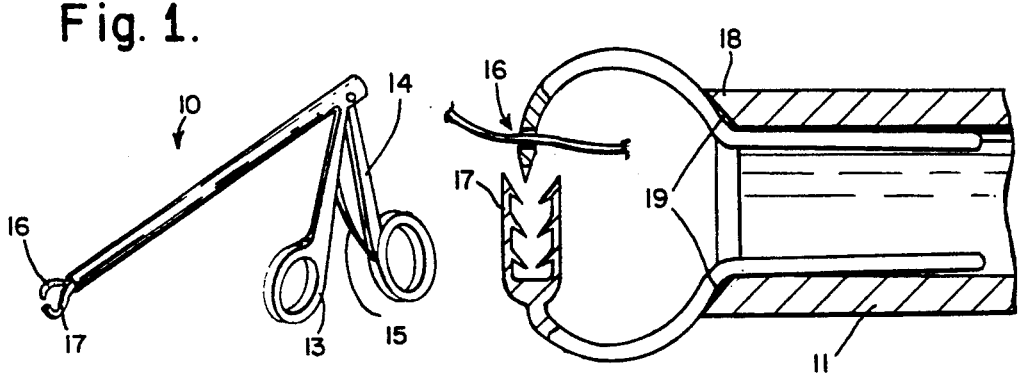
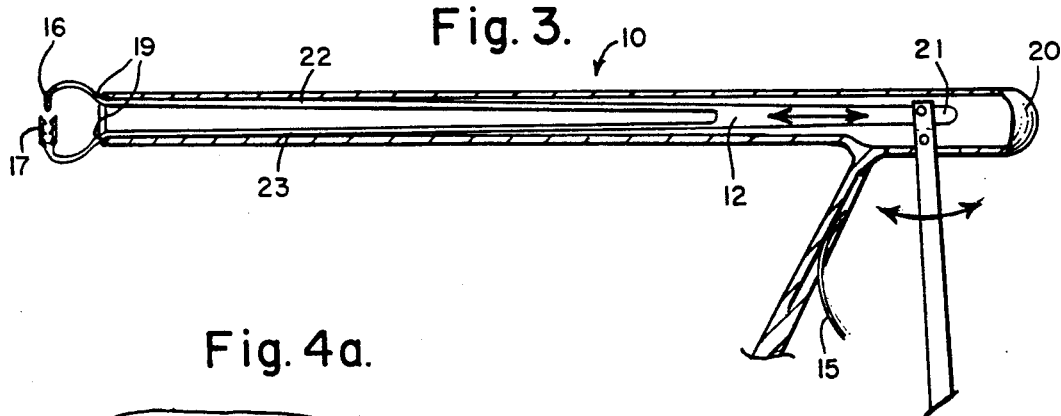
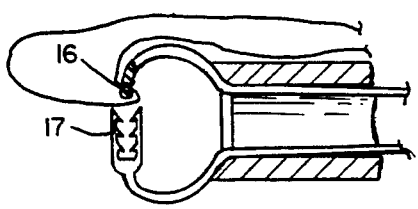
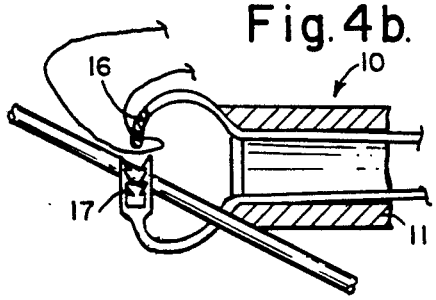
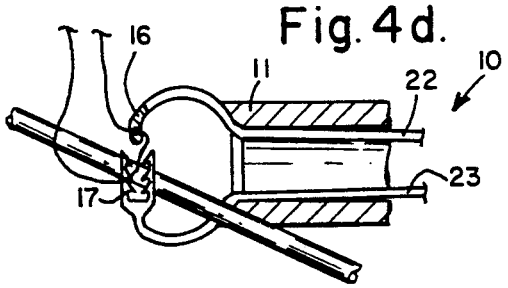
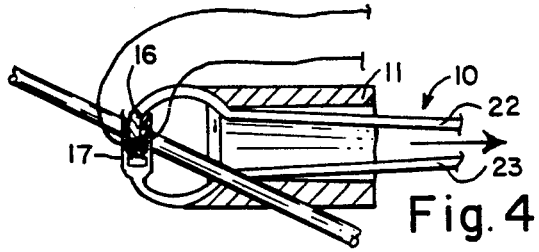
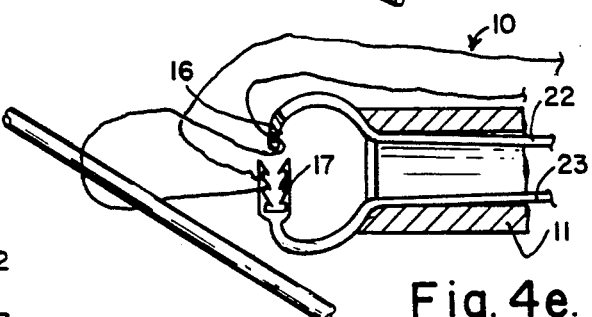

SUTURE LIGATING DEVICE FOR USE WITH AN ENDOSCOPE

BACKGROUND OF THE INVENTION

1. Field of the Invention

The invention relates to a suture ligating device which may be handled in an uncomplicated manner and more particularly to a suture ligating device which allows rapid and reliable tying of threads for individual stitches in body cavities through a long endoscopic tube.

2. Description of the Prior Art

U.S. Pat. No. 4,683,885, entitled Applicator for tying sewing threads, issued to Frieder Hutterer, Gerd Buess and Manfred Boebel on Aug. 4, 1987, teach an applicator which is for use in tying sewing threads in combination with an endoscope tube. The applicator includes a coil connected to a longitudinal passage through a shaft and including hollow turns connected to the shaft passage for reception of a sewing thread, whose proximal extremity is passed through a loop projecting from a radial opening at the distal extremity of the shaft, is then drawn through the shaft passage and fastened to the proximal shaft extremity. Tying the single stitch after piercing the tissues is performed by passing the needle axially through the coil and then around the thread and twisting the coil out of the loop formed thereby to form the first half of a knot which is then complemented by the second half of the knot tied in the same way, the knot being tied by subsequently pulling together the two said halves. The applicator may be utilized with an endoscope tube, for example as shown in the German patent specification No. 3319049, so that the thread led through the coil and shaft may be offered up together with the needle to the wound which is to be stitched, to which end the wound walls are pierced by the needle using a needle holder which is also led through the endoscope tube, both under observation. Drawing a thread provided with a needle into the applicator is performed prior to the insertion of the applicator through the endoscope tube into the bodily cavity space.

U.S. Pat. No. 4,957,498, entitled Arthroscopic suturing instrument, issued to Richard B. Caspari, Arthur F. Trott and F. Bays on Sep. 18, 1990 teaches a suturing instrument for use in arthroscopic surgery which includes a hollow needle for penetrating tissue to be sutured within the body while the tissue is clamped between relatively movable jaws, and a suture feed mechanism for feeding suture material through the hollow needle such that the jaws can be opened and the suturing instrument withdrawn from the body pulling the free end segment of the suture material with the instrument. A knot can be tied in the suture material externally of the body and the knot moved back into the body at a position adjacent the tissue.

U.S. Pat. No. 3,570,497 teaches a suture apparatus which includes a cord of latch notches, a needle at one end of the cord, and a latch collar at the other end of the cord. The latch collar is provided with a passage through which the needle is pulled, followed by a selected number of latch notches. Upon the pulling of a final notch through the collar passage, the cord is severed on a side of the latch collar opposite the side of entry of the cord into the latch passage. Although the suture apparatus provides a number of advantages over simple suture threads, that suture device has several shortcomings which make it unsuitable for many surgical applications. Particularly in cases requiring fine stitches or ligatures, where this suture device is necessarily small, the needle and cord of that device are inserted through the passage in the latch collar only with appreciable difficulty. Although in some applications, such as in the binding of a sternum or the approximating of ribs, a large suture device is necessary to provide the requisite strength, in either applications complications may arise by leaving a large suture structure at the surgical site. Different techniques are known for stitching wounds in bodily cavities by means of a thread which has to be tied. These however require difficult manipulations with needle and thread under considerable expenditure of patience and time and a specific routine.

U.S. Pat. No. 4,069,825 teaches a ligature which includes a surgical thread with a plurality of spherical or conical projections spaced regularly along the length of the thread. One end of the thread is attached to a cylindrical member having an aperture with a diameter larger than the outside diameter of the projections on the thread. The spacings between the projections and the size of the apertured member are designed to enable a locking of the thread in a loop about a vessel by means of friction forces which arise between the projections and the apertured member upon a passing of the thread through the aperture and a subsequent tightening of the loop so formed. This ligature suffers from the same disadvantages as the suture apparatus of U.S. Pat. No. 3,570,497. Basically, in cases where fine blood vessels or other ducts are to be closed, the passing of the thread through the apertured member is difficult and requires considerable concentration and patience.

U.S. Pat. No. 3,985,138 teaches a ligature which includes an endless loop formed with a continuous series of ratchet-like ridges or pawl-like teeth. One side of the loop is connected via an elongate extension to a finger engaging loop, the extension traversing an opening in a closure member. Upon a pulling of the ridged loop through the closure by means of the finger engaging loop, the ridged loop is constricted and the teeth along the endless loop are caught against the closure to lock the endless loop in its constricted configuration. Although this ligature obviates the problem of passing the thread through a small opening, the endless ridged or toothed loop must generally be passed over the end of a hemostat prior to closure of that loop about a severed blood vessel. This step clearly complicates the ligation procedure. In addition, the closure of this ligature is necessarily bulky.

U.S. Pat. No. 4,621,640, entitled Mechanical needle carrier and method for its use, issued to James S. Mulhollan and Lionel Starr on Nov. 11, 1986, teaches a mechanical needle carrier is provided which can grasp and carry a surgical needle through a cannula, position the needle and set a stitch at the remote location and then release the needle and be withdrawn from the cannula.

U.S. Pat. No. 4,602,635 Remote Surgical Knot Tier and Method of Use, issued to James S. Mulhollan and Lionel Starr on Jul. 29, 1986, teaches a remote surgical knot tier which can hold, push and place loops forming a knot in suture material from a manipulation area into a remote site in the body of a human being or an animal through a puncture wound or other small opening.

U.S. Pat. No. 4,596,249 entitled Implement for Setting Sutures, issued to Vincent J. Freda and Henry Puchalski on Jun. 24, 1986, teaches an implement for setting sutures which is particularly suitable for use in situations where access to the tissue to be sutured is difficult. The implement includes a pair of hinged arms, each having a handle portion and a jaw portion. The tip of one jaw has a tissue piercing hook and the tip of the other jaw has a notch or opening through which the hook may pass. A series of guides and openings position the suture above the opening for engagement by the hook. When the jaws are closed about the tissue, the hook will pass through the tissue and the suture will ride around the hook. The suture will be engaged by the hook and upon opening the jaws, the hook will pull a loop of suture through the tissue, the loop may then be cut and the suture fixed in the usual manner.

U.S. Pat. No. 4,493,323, entitled Suturing Device and Method for Using Same, issued to John P. Albright, Robert K. Martin and John A. Dyson on Jan. 15, 1985, teaches a suturing device which includes an elongated tube which is adapted to be inserted into the body so that its internal end is positioned adjacent the tissue which is to be sutured. A plunger is sized to slide within the tube and includes at one end a grasping mechanism for releaseably grasping a pair of needles in spaced-apart relation to one another. The plunger is fitted within the tube and the needles are forced outwardly through the lower end of the tube so that they penetrate and extend through the tissue to be sutured. The needles are forced through the tissue to be sutured and are forced outwardly through the skin layer of the patient so that they can be grasped and pulled from the releaseable grasping mechanism of the plunger.

U.S. Pat. No. 4,981,149, entitled Method for Suturing with a Bioabsorbable Needle, issued to InBae Yoon and Samuel C. Yoon on Jan. 1, 1991, teaches suture devices, primarily for use in endoscopic surgery, which include a suture needle made of bioabsorbable material for pulling a length of suture material through bodily tissue allowing the suture needle to be either inadvertently or intentionally left in the tissue, and a suture needle having a length of suture material attached thereto with a contractible loop or passage at the proximal end of the suture material to allow the suture needle to be passed therethrough, the loop or passage contracting to clamp or grip the suture material to function similar to a conventional tied suture knot.

U.S. Pat. No. 4,235,238, entitled Apparatus for Suturing Coeliac Tissues, issued to Hisao Ogiu and Hideki Shimonaka on Nov. 25, 1980, teaches a coeliac tissue-suturing apparatus which includes a flexible tubular member having a passage extending therethrough and inserted into a channel of an endoscope and a needle having one end concentrically fixed to that end of the tubular member which is inserted into the endoscope and having the other end made into a sharp tip. The needle has substantially the same outer diameter as the tubular member and adapted to protrude from a distal end of the endoscope, a first-stop receiving chamber communicating with the atmosphere and the passage of the tubular member, a first stop for setting suturing thread on tissues around a coeliac bleeding spot at the commencement of a suturing operation, said first stop being adapted to fix one end of the suturing thread extended along the tubular member, and normally received in the first-stop receiving chamber, and a pushing member inserted into the tubular member for pushing the first stop out of the first stop-receiving chamber.

U.S. Pat. No. 4,932,962, entitled Suture Devices Particularly Useful in Endoscopic Surgery and Methods of Suturing, issued to InBae Yoon and Samuel C. Yoon on Jun. 12, 1990, teaches suture devices, primarily for use in endoscopic surgery, which include a suture needle made of bioabsorbable material for pulling a length of suture material through bodily tissue allowing the suture needle to be inadvertently or intentionally left in the tissue, and a suture needle having a length of suture material attached thereto with a contractible loop or passage at the proximal end of the suture material to allow the suture needle to be passed therethrough, the loop or passage contracting to clamp or grip the suture material to function similar to a conventional tied suture knot. The suture device relates to a suturing apparatus conducted into a body cavity through an endoscope to suture tissues around a bleeding portion in the body cavity. Suturing of bodily tissue is a time consuming part of most surgical procedures including both open surgery and endoscopic or closed surgery. By open surgery is meant surgery wherein the surgeon gains access to the surgical site via a relatively large incision, and by endoscopic surgery is meant surgery wherein the surgeon gains access to the surgical site via one or more portals through which endoscopes are introduced to view the surgical sire and through which instruments, such as forceps, cutters, applicators and the like, are introduced to the surgical site. There are many common endoscopic surgical procedures, including arthroscopy, laprascopy, for example. In the past, suturing has been accomplished with the use of a sharp metal suture needle attached to the end of a length of suture material, the suture needle being caused to penetrate and pass through the tissue pulling the suture material through the tissue. Once the suture material has been pulled through the tissue, the surgeon ties a knot in the suture material, the knotting allowing the surgeon to adjust the tension on the suture material to accommodate the particular tissue being sutured and control approximation, occlusion, attachment or other conditions of the tissue. The ability to control tension is extremely important to the surgeon regardless of the type of surgical procedure being performed; however, knotting of the suture material is time consuming and tedious work, particularly in microsurgery and endoscopic surgery. That is, in microsurgery suturing is necessarily time consuming due to the small size of the suture needle and the suture material and the concomitant difficult manipulation required to pass the suture material. With respect to endoscopic surgery, suturing tying knots represents an even more time consuming procedure due to the difficult maneuvers required. Accordingly, while endoscopic surgery would be preferred for most procedures, the advantages are often outweighed by the disadvantages caused by the length of time required to complete the endoscopic surgical procedure, which time is greatly extended due to the time required for suturing. Another disadvantage of suturing with a metal suture needle and suture material during endoscopic surgery is that the suture needle and suture material is difficult to hold and manipulate and can be easily dropped. Should the surgery needle be dropped, open surgery with its attendant disadvantages must be performed to find and remove the needle.

There have been many attempts to provide devices to take the place of conventional suturing with a suture needle and a length of material; however, such prior art devices have essentially been staples, clips, clamps or other fasteners not providing the adjustable tension obtained by the surgeon while knotting a length of suture material. U.S. Pat. No. 3,827,277, U.S. Pat. No. 4,060,089, U.S. Pat. No. 4,490,326, U.S. Pat. No. 4,513,746, U.S. Pat. No. 4,532,926, U.S. Pat. No. 4,458,202, U.S. Pat. No. 4,573,469, U.S. Pat. No. 4,590,937, U.S. Pat. No. 4,595,007, U.S. Pat. No. 4,602,634, U.S. Pat. No. 4,646,741, U.S. Pat. No. 4,671,280, U.S. Pat. No. 4,719,917, U.S. Pat. No. 4,741,337 teach representative prior art devices for use in place of conventional suturing. Many of these prior art devices are made of bioabsorbable materials such that the devices are absorbed over time into the bodily tissue and do not have to be removed after the bodily tissue has healed. Different techniques are known for stitching wounds in bodily cavities by means of a thread which has to be tied. These however require difficult manipulations with needle and thread under considerable expenditure of patience and time and a specific routine. Endoscopic surgery is preferred over open surgery due to the greatly reduced trauma and wound healing for the patient due to concomitant cost savings associated with shorter hospital stays and performing surgery without general anesthesia and in non-hospital or out-patient surgery sites.

Accordingly, there has been much effort spent to develop techniques for facilitating the suturing normally performed by use of a metal suture needle and a length of suture material. Alternative techniques proposed have included electrical coagulation, mechanical devices such as clips, clamps and staples, and lasers; however, no well accepted alternative has yet been found in that suturing and tying are essential and vital parts of most surgical procedures. That is, to date the proposed alternatives have had disadvantages, including increased risk to the patient, while not providing the surgeon with the advantages of suturing and tying and not being useful in a wide range of procedures to allow expansion of the areas in which endoscopic surgery can be effectively performed. Thus, there is a great need for suture devices, particularly useful in endoscopic surgery, that allow surgeons to suture and tie knots in a manner with which they are familiar without undue concern as to the loss of the suture needle and further for suture devices that allow controlled approximation of tissue and tying to produce controlled tension.

U.S. Pat. No. 4,935,027, entitled Surgical Suture Instrument with Remotely Controllable Suture Material Advancement, issued to Inbae Yoon on Jun. 19, 1990, teaches surgical instruments and methods which effect suturing of tissue that ca be controlled from a position remote from the suture site. A continuous feed of suture material is provided through opposed forceps jaw members between which the tissue segments are interposed to expedite the suturing process and enable suturing to be accomplished at remote internal sites of the body incident to various endoscopic procedures.

SUMMARY OF THE INVENTION

In view of the foregoing factors and conditions which are characteristic of the prior art it is the primary object of the present invention to provide for a suture ligating device which may be handled in an uncomplicated manner and which allows of reliable and rapid tying of threads for individual stitches in body cavities through a long endoscopic tube.

In accordance with an embodiment of the present invention a suture ligating device for use with an endoscope is described. The suture ligating device includes a long hollow tube and an elongated, integral member, a resiliently-biased scissoring mechanism, a suture carrying mechanism and a suture grasping mechanism. The long hollow tube has a open end which has a inwardly beveled edge and a closed end and is adapted to be slidably inserted into the endoscope. The elongated, integral member is adapted to be slidably inserted into the long hollow tube through the open end and is shaped like a fork having a stem having a first end and a second end. A first elongated prong has a first end and a second end. A second elongated prong has a first end and a second end. The first and second prongs are joined at the respective first ends thereof to the stem at its first end. One scissor arm of the resiliently-biased scissoring mechanism is fixedly coupled to the long hollow tube at its closed end and the other scissor arm is pivotally coupled to the long hollow tube at its closed end in order to be able retract the elongated integral member from a first position. The suture grasping mechanism and the suture carrying mechanism are mechanically coupled to the first and second prongs at their second ends and are aligned so that they become engaged when the elongated, integral member is retracted from the first position to a second position so that a slip knot can be tied externally to the endoscope.

The features of the present invention which are believed to be novel are set forth with particularity in the appended claims.

Other claims and many of the attendant advantages will be more readily appreciated as the same becomes better understood by reference to the following detailed description and considered in connection with the accompanying drawing in which like reference symbols designate like parts throughout the figures.

DESCRIPTION OF THE DRAWING

FIG. 1 is a perspective view of a suture ligating device which has been constructed in accordance with the principles of the present invention.

FIG. 2 is a longitudinal view in cross-section of the suture ligating device of FIG. 1 which includes a long hollow tube and an elongated, integral member and a resiliently-biased scissoring mechanism.

FIG. 3 is a partial, enlarged longitudinal view in cross-section of the suture ligating device of FIG. 1 which includes suture carrying mechanism and a suture grasping mechanism.

FIG. 4a is a partial, enlarged longitudinal view in cross-section of the suture ligating device of FIG. 1 in a first position passing a suture into a body cavity.

FIG. 4b is a partial, enlarged longitudinal view in cross-section of the suture ligating device of FIG. 1 in the first position passing a suture around a vessel within the body cavity.

FIG. 4c is a partial, enlarged longitudinal view in cross-section of the suture ligating device of FIG. 1 in a second position with the suture around the vessel within the body cavity.

FIG. 4d is a partial, enlarged longitudinal view in cross-section of the suture ligating device of FIG. 1 in the first position with the suture around the vessel within the body cavity.

FIG. 4e is a partial, enlarged longitudinal view in cross-section of the suture ligating device of FIG. 1 in the second position so that the suture ligating device

DESCRIPTION OF THE PREFERRED EMBODIMENT

In order to best understand the present invention it is necessary to refer to the following description of its preferred embodiment in conjunction with the accompanying drawing. Referring to FIG. 1 a suture ligating device 10 for use with an endoscope includes a long hollow tube 11 and an elongated, integral member 12, a first scissor arm 13, a second scissor arm 14 and a spring 15, a suture carrying mechanism 16 and a suture grasping mechanism 17. The long grasping mechanism 17. The long hollow tube 11 has a open end 18 which has a inwardly beveled edge 19 and a closed end 20 and is adapted to be slidably inserted into the endoscope. The elongated, integral member 12 is adapted to be slidably inserted into the long hollow tube 11 through the open end 18 and is shaped like a fork having a stem 21 having a first end and a second end. A first elongated prong 22 has a first end and a second end. A second elongated prong 23 has a first end and a second end. The first and second prong 22 and 23 are joined at the respective first ends thereof to the stem 21 at its first end. The first scissor arm 13 is fixedly coupled to the long hollow tube at its closed end. The second scissor arm 14 is pivotally coupled to the long hollow tube 11 at its closed end and which is adapted to retract the elongated, integral member 12 from a first position. The spring resiliently biases the second scissor arm 14 with respect to the first scissor arm 13 so that the elongated, integral member 12 is normally in the first position. The suture carrying mechanism 16 carries a suture and is mechanically coupled to the first prong 22 at the second end thereof. The suture grasping mechanism 17 grasps the suture and is mechanically coupled to the second prong 23 at the second end thereof. The suture grasping mechanism 17 and the suture carrying mechanism 16 are aligned so that they become engaged when the elongated, integral member 12 is retracted from the first position to a second position.

Referring to FIGS. 4a through 4e in conjunction with FIG. 2 and FIG. 3 the suture ligating device 10 is in the first position while passing a suture into a body cavity through an endoscope. Referring to FIG. 4a the suture ligating device 10 is in the first position while passing a suture into a body cavity through an endoscope. Referring to FIG. 4b the suture ligating device 10 is in the first position while passing a suture around a vessel within the body cavity. Referring to FIG. 4c the suture ligating device 10 is in the second position with the suture around the vessel within the body cavity. Referring to FIG. 4d the suture ligating device 10 is in the first position with the suture around the vessel within the body cavity. Referring to FIG. 4e the suture ligating device 10 is in the second position so that the suture ligating device 10 with the suture around the vessel within the body cavity.

From the foregoing it can be seen that a suture ligating device for use with an endoscope has been described. It should be noted that distances of and between the figures are not to be considered significant.

Accordingly it is intended that the foregoing disclosure and showing made in the drawing shall be considered only as an illustration of the principles of the present invention.

What is claimed is:
1. A suture ligating device for use with an endoscope, said suture ligating device comprising:
   a. a long hollow tube which has a open end and a closed end and which is adapted to be slidably inserted into the endoscope, said open end having a inwardly beveled edge;
   b. an elongated, integral member which is adapted to be slidably inserted into said long hollow tube and which is shaped like a fork having a stem having a first end and a second end, a first elongated prong having a first end and a second end and a second elongated prong having a first end and a second end, said first and second prongs being joined at said respective first ends thereof to said stem at its said first end;
   c. a first scissor arm which is fixedly coupled to said long hollow tube at its said second closed end;
   d. a second scissor arm which is pivotally coupled to said long hollow tube at its said second closed end and which is adapted to retract said elongated, integral member from a first position;
   e. resilient biasing means for resiliently biasing said second scissor arm with respect to said first scissor arm so that said elongated, integral member is normally in said first position;
   f. suture carrying means for carrying a suture, said suture carrying means being mechanically coupled to said first prong at said second end thereof;
   g. suture grasping means for grasping the suture, said suture grasping means being mechanically coupled to said second prong at said second end thereof whereby said suture grasping means and suture carrying means are aligned so that they become engaged when said elongated, integral member is retracted from said first position to a second position so that a slip knot can be tied externally to the endoscope.

* * * * *